United States Patent [19]

Comparetto et al.

[11] 4,360,428
[45] Nov. 23, 1982

[54] INVERTED VORTEX, PARTICLE SEPARATION CHAMBER

[76] Inventors: John E. Comparetto, P.O. Box 408; Robert L. Brand, P.O. Box 214 both of Chincoteague, Va. 23336

[21] Appl. No.: 145,556

[22] Filed: May 1, 1980

[51] Int. Cl.³ .............................................. B01D 19/00
[52] U.S. Cl. .................................... 210/188; 210/218; 210/416.1; 210/512.3; 55/204; 55/190; 433/92
[58] Field of Search ................ 210/787, 788, 218–220, 210/304, 311, 512.3, 416.1, 188; 55/203, 204, 52, 190, 55; 433/92

[56] References Cited

U.S. PATENT DOCUMENTS

| | | | |
|---|---|---|---|
| 2,376,221 | 5/1945 | Baker | 55/52 |
| 3,616,601 | 11/1971 | Senkewich | 55/190 |
| 3,804,255 | 4/1974 | Speece | 210/221.2 |
| 3,850,810 | 11/1974 | Teodoroiu | 210/219 |
| 3,928,003 | 12/1975 | Fryar | 55/190 |
| 3,933,640 | 1/1976 | Kirk et al. | 210/219 |
| 3,941,695 | 3/1976 | Harris | 210/219 |
| 3,996,027 | 12/1976 | Schnell et al. | 55/52 |
| 4,000,227 | 12/1976 | Garrett | 210/219 |
| 4,209,359 | 6/1980 | Sethy | 55/52 |

Primary Examiner—Benoît Castel

[57] ABSTRACT

An inverted fluid vortex is created by an impeller within an inverted funnel. Heavier than water particles are forced outward and downward by the interplay of centrifugal, centripetal, gravitational forces and the internal downward cant of a funnel. A vortical fluid apex is suctioned from the system as necessary to keep the volume of the vacuum portion of the system constant and therefore the vacuum pressure constant.

2 Claims, 4 Drawing Figures

INVERTED VORTEX, PARTICLE SEPARATION CHAMBER

BACKGROUND OF THE INVENTION

In dentistry, vacuum systems are used to remove water, saliva, and debris from the patient's mouth. This fluid effluent often includes valuable materials such as amalgam from old amalgam fillings that are being removed. In Application Ser. No. 132,051 filed Mar. 20, 1980, now abandoned in favor of continuation Ser. No. 311,106 filed Oct. 13, 1981, the fluid effluent with its particulate matter was removed to a chamber comprising an upper vacuum layer and a lower liquid layer. The particles in the effluent would then settle to the bottom of the chamber. However, some of the finer particulate matter is held suspended in the liquid phase. In order to separate the liquid from this particulate matter, atomization of the fluid portion could be accomplished by various means enumerated in this first application. To sustain an even vacuum pressure on the oral cavity as well as on the upper portion of this chamber the upper gaseous layer should have an approximately constant volume. This is accomplished by introducing fluid particles free of particulate matter into the gaseous space where the outgoing vacuum duct removes this fluid portion from the upper layer into which it has been dispersed. Various means for accomplishing the dispersion of the fluid phase into the gaseous segment were designated in the earlier application. Among these were ultrasonic heads, as well as, conventional atomization means. The conventional atomization means would include a nozzle into which both air and fluid from the bottom of the chamber would be introduced. There are many mechanisms of increasing the dispersion of fluid propelled by air source such as stream splitters, spinning discs, and gratings. The air pressure source in the foregoing would have to be of such a relatively diminutive force that it would not interfere with the overall suction from oral cavity to the vacuum drainage.

DETAILED DESCRIPTION OF THE INVENTION

Figure 3:
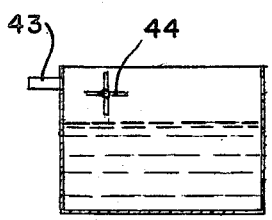
FIGS. 3 and 4 are diagramatic views of a paddle mechanism in a separation chamber.
Figure 4:
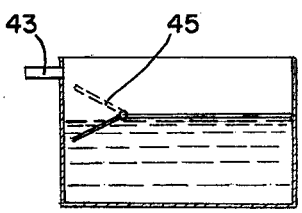

Another method of dispersing fluid into the upper gaseous chamber would be a paddle mechanism 44 of FIG. 3, that splashes the water at the interface causing some of the splashed water to be pulled up by the vacuum outlet 43. The paddle mechanism would be close to the vacuum outlet port for easy access of splashed surface water to the vacuum outlet. The paddle could be on a wheel or be an up and down splashing lever 45 of FIG. 4, that strikes the water like a beaver's tail.

Figure 1:
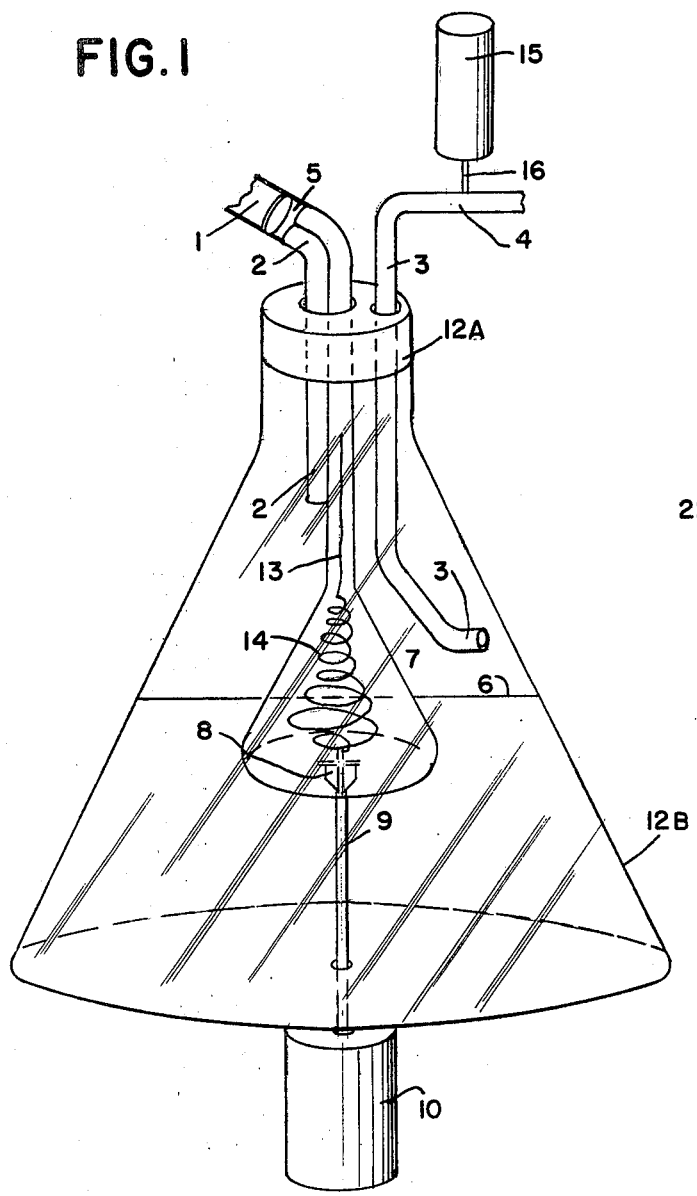
FIG. 1 is a diagramatic view of an inverted funnel-impeller suction separation chamber.

In FIG. 1 separation chamber 12B is the shape of an Erlenmeyer flask. It is tightly stoppered at 12A. The common suction duct 1 splits into suction duct 2 and 5. Suction duct 2 exerts its pressure on the upper gaseous section of the separatory chamber and, therefore, on suction duct 3 which exits the stopper 12A and travels to the oral cavity where fluid effluent 4 is removed to enter the upper portion of the separatory chamber. A liquid-gas interphase 6 is formed between the upper gaseous section and the lower liquid section. The inverted funnel structure 7 is submerged into the fluid section of the separatory chamber. Impeller 8 spins on axle 9 driven by motor 10 to cause a vortex swirl of water within the inverted funnel 7. Because the desirable fluid effluent particles of gold and amalgam are heavier in mass than a given volume of water, any particles that have not had time to settle out in the fluid portion of the chamber will be spun by the vortex created by the impeller to the sides of funnel 7 and downward by the funnel cant. The particle free fluid 13 is driven upward toward the apex of the funnel to be suctioned off through tubing 5. An accessory apparatus that may be desirable under certain conditions would be detergent chamber 15 and a micropipette tubing 16. The pressure head from the small lumen with the micropipette tubing 16 would be of such a nature to allow only small quantities of detergent to be introduced into suction tube 3 at some point between the oral cavity and the separation chamber. The detergent's sudsing ability could be of variable strength. Sudsing could also be varied with conditions. The flow rate of the detergent through micropipette 16 could be varied with the aperture as well as the suction pressure and effluent flow rate. Sudsing would occur by the agitation of the impeller. The speed of the impeller would also be a variable that could effect sudsing. The motor mechanism and impeller mechanism could be an agitator type of propeller with an agitating type of oscillating movement rather than the rotary movement used to form a vortex. In this case, the fluid phase is removed via controlled sudsing; the suds being free of amalgam or gold particles.

Figure 2:
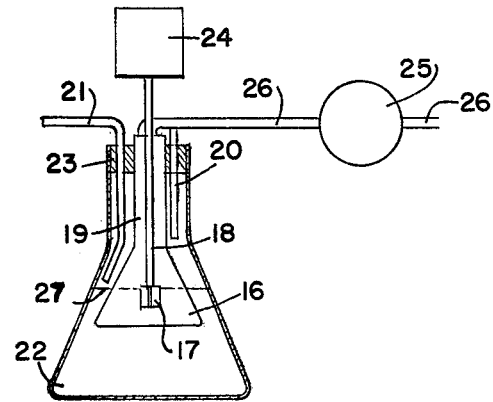
FIG. 2 is a diagramatic view of an alternate impeller deployment.

FIG. 2 is a variation of deployment of an impeller or agitator. Impeller 17 is within the fluid phase of separation chamber and is also within the inverted funnel. Around the impeller or agitator axis 18 is suction tube 19. Suction tube 20 applies negative suction pressure to the upper gaseous section of the separation chamber and thusly suction tube 21 that exits the suction chamber through stopper 23. The fluid effluent is pulled from the oral cavity through tube 21 entering the upper portion of the separation chamber where it falls into the fluid phase. Common suction duct 26 exerts pressure on both 19 and 20. Particle free fluid effluent goes up section 19 as it did section 5 in FIG. 1. The effluent enters tube 26 where it is vented into sewer drainage from vacuum motor 25. The impeller motor is designated as 24. The fluid section is designated as 22 with an interface 27. A detergent drip could also be utilized in this last system by introducing the detergent through tubing 21 between the separation chamber and oral cavity as was done in the previous example.

From the foregoing description, one skilled in the art can easily ascertain the essential characteristics of this invention and without departing from the spirit and scope thereof, can make various changes and modifications of the invention to adapt to its various usages and conditions.

What is claimed is:

1. An apparatus for separating a particle-laden effluent stream comprising a trapezoidal or conical shaped chamber having an upper gaseous portion and a lower liquid portion, a liquid-gas interphase being formed between the upper and lower portions, a liquid inlet within the upper gaseous portion which supplies particle-laden liquid for the apparatus for separation, a gas outlet within the upper gaseous portion which exerts a vacuum pressure so as to remove gas and liquid vapor, an inverted funnel means which is partially submerged in the lower liquid portion, and partially suspended in the upper gaseous portion, an impeller means within the funnel means, the impeller means forming a fluid vortex within the funnel means, the fluid vortex causing particulate matter in the liquid in the funnel means to be driven downward along an internal downward cant of the funnel means into the lower liquid portion below the funnel means and the fluid vortex causing particulate-free liquid to be driven upward into the upper portion of the inverted funnel means, and a liquid outlet located in the upper portion of the inverted funnel means which removes the particulate-free liquid from the apparatus.

2. the apparatus of claim 1 further comprising a detergent injecting means fluidly connected to the apparatus.

* * * * *